(12) United States Patent
Hilfiker et al.

(10) Patent No.: US 8,828,417 B2
(45) Date of Patent: Sep. 9, 2014

(54) BIOACTIVE COATING FOR AN IMPLANTABLE DEVICE OR BIOPROSTHESIS

(75) Inventors: Andres Hilfiker, Hannover (DE); Denise Hilfiker-Kleiner, Hannover (DE); Artur Lichtenberg, Duesseldorf (DE)

(73) Assignee: Corlife OHG, Hannover (DE)

( * ) Notice: Subject to any disclaimer, the term of this patent is extended or adjusted under 35 U.S.C. 154(b) by 290 days.

(21) Appl. No.: 12/672,590

(22) PCT Filed: Jul. 8, 2008

(86) PCT No.: PCT/EP2008/005556
§ 371 (c)(1),
(2), (4) Date: Feb. 2, 2011

(87) PCT Pub. No.: WO2009/018888
PCT Pub. Date: Feb. 12, 2009

(65) Prior Publication Data
US 2011/0117163 A1    May 19, 2011

(30) Foreign Application Priority Data

Aug. 6, 2007 (EP) .................................. 07015359

(51) Int. Cl.
*A61F 2/00* (2006.01)
*A61L 27/22* (2006.01)
*A61L 27/34* (2006.01)
*A61L 27/54* (2006.01)

(52) U.S. Cl.
CPC ............... *A61L 27/34* (2013.01); *A61L 27/227* (2013.01); *A61L 2300/606* (2013.01); *A61L 27/54* (2013.01)
USPC ........... 424/423; 435/378; 435/379; 530/350; 514/19.1; 514/21.92

(58) Field of Classification Search
CPC . A61L 27/34; A61L 2300/606; A61L 27/227; A61L 27/54

USPC ................... 424/423; 435/378, 379; 530/350; 514/19.1, 21.92
See application file for complete search history.

(56) References Cited

U.S. PATENT DOCUMENTS

| 5,192,312 A | 3/1993 | Orton | |
|---|---|---|---|
| 2011/0244014 A1* | 10/2011 | Williams et al. | 424/422 |

FOREIGN PATENT DOCUMENTS

| CN | 1174573 A | 2/1998 |
|---|---|---|
| CN | 1835763 A | 9/2006 |
| CN | 1835763 A | 9/2006 |
| JP | 2003-527170 A | 9/2003 |
| JP | 2003-531685 A | 10/2003 |
| JP | 2004-528929 A | 9/2004 |
| JP | 2005-287409 A | 10/2005 |
| WO | 01/49827 A1 | 7/2001 |
| WO | 01/82992 A1 | 11/2001 |
| WO | 02/098475 A1 | 12/2002 |
| WO | 2005/040191 A2 | 5/2005 |

OTHER PUBLICATIONS

Brigstock "The CCN family: a new stimulus package," Journal of Endocrinology (2003) 178, 169-175.*
Lichtenberg et al. "In vitro re-endothelialization of detergent decellularized heart valves under simulated physiological dynamic conditions," Biomaterials 27 (2006) 4221-4229.*

* cited by examiner

*Primary Examiner* — Suzanne Ziska
(74) *Attorney, Agent, or Firm* — Whitham, Curtis, Christofferson & Cook, P.C.

(57) ABSTRACT

For an implantable device intended for use in the human body an in-vivo colonization with autologous cells is often desired. The devices, especially prosthetic devices like implant tissues, grafts, shunts, vessels, organs or a part of organs are commonly derived from animal or human origin and comprise a collagen-based tissue matrix. The invention proposes a coating deposited on a surface of the device and comprising the matrix protein CCN1 as an extracellular matrix-associated protein mediating cell adhesion or cell migration.

22 Claims, No Drawings

200
BIOACTIVE COATING FOR AN IMPLANTABLE DEVICE OR BIOPROSTHESIS

The present invention relates generally to implantable devices and more particularly to a coating for an implantable device, said device and a method to generate the device. The invention is especially suited to produce decellularized and subsequently coated bioprosthetic devices on a collagen matrix basis.

BACKGROUND OF THE INVENTION

The ability to replace or repair deseased arteries, heart valves, venes or other soft tissues with bioprosthetic devices has provided surgeons with a method of treating valve deficiencies due to disease and congenital defects and other severe complications.

Typical procedures involve
the removal of the natural valve and surgical replacement with a bioprosthetic valve;
the removal of natural arteries or venes and surgical replacement with bioprosthetic arteries or venes;
the implantation of bioprosthetic shunts;
the remodeling of biological structures with vascularised matrices such as trachea using a decellularized intestinal matrix.

Following implantation, there is a high risk of postoperative thrombosis, calcification or infection.

With respect to replacement of biological structures by bioprosthetic grafts, care must be taken to ensure confluent coverage of the surface with endothelial cells. For example, to achieve an endothelial cell layer on the heart valve, decellularized biological heart valves are cultivated with endothelial cells in bioreactors. These techniques, however, are complicated, time consuming and susceptible to contamination and therefore have limited effectiveness.

U.S. Pat. No. 5,192,312 discloses an allograft or xenograft treated with a growth factor (bFGF) and incubated with cells (fibroblasts) that migrate and proliferate in response to the growth factor. Although viability and longevity could be improved and degeneration of the implant could be decreased or slowed, allergic complications and adverse immune reaction could only be avoided with autogenous cells that are not always available.

It is therefore one object of the invention to provide a non- or reduced immunogenic bioartificial transplant readily available. Another object of the invention is to provide an implantable device or prosthesis that is more easily repopulated or remodeled in-vivo with endothelial cells of the recipient. Yet another object is to facilitate the use of xenografts and circumvent the low supply of homografts, especially for pediatric patients.

SUMMARY OF THE INVENTION

In contrast to the in-vitro technologies used in the state of the art to cover bioprosthetic devices with endothelial cells, one aspect of the present invention includes a coating of the prosthesis with CCN1 as a bioactive molecule, to enhance the overall repopulation of the implantable device with endothelial cells in situ. The CCN1-treated device greatly enhances colonization with endothelial cells and therefore enhances also the overall biocompatibility of the device.

Thus, to solve the objects of invention there is in general provided a coating for an implantable device, said implantable device being intended for use in the human body where in-vivo repopulation or remodeling with own, i.e. autologous cells of a recipient is desired and expected, the coating being characterized in that it comprises an extracellular matrix-associated protein ("matrix protein") mediating cell adhesion or cell migration and preferably also enhancing growth-factor stimulated cell proliferation or a fragment of this protein or a construct with this protein, each with corresponding basic function with respect to cell adhesion compared to CCN1 as standard, deposited on a surface of the device.

Preferably, the extracellular matrix-associated protein is a member of the CCN family, most preferably it is CCN1.

The ability of the extracellular matrix-associated protein to mediate cell adhesion or cell migration or to enhance a growth-factor-stimulated cell proliferation can be tested, for example in the following manner: cells are seeded in vitro to a test piece of a tissue or implant material under exactly the same conditions but with and without a coating of the extracellular matrix-associated protein to be tested. The cell adhesion should be improved by at least 20%, i.e. the density of cells on the surface after a certain period of cultivation should be at least 20% higher than for the comparative sample.

CCN1 also named Cysteine-rich angiogenic inducer, 61 (CYR61), GIG1, or Insulin-like growth factor-binding protein 10 (IGFBP10). CCN1 is a protein with a molecular weight of 42 kDa, composed of 381 amino acids, thereof 36 cysteins. CCN1 is an extracellular matrix protein that binds integrins and heparin. CCN1 promotes i.a. the cell proliferation, chemotaxis, angiogenesis, and cell adhesion. CCN1 appears to play a role in wound healing by up-regulating the expression of a number of genes involved in angiogenesis, inflammation and matrix remodeling in skin fibroblasts. This up-regulation includes VEGA-A, VEGA-C, MMP1, MMP3, TMP1, uPA, PAI1 and integrins alpha-3 and alph-5, whereas the expression of alpha-1 and alpha-2 subunits of collagen type-1 is down-regulated. CCN1-mediated gene regulation is dependent on heparin-binding. CCN1 promotes cell adhesion and adhesive signaling through integrin alpha-6/beta-1, cell migration through integrin alpha-v/beta-5 and cell proliferation through integrin alpha-v/beta-3 interactions. CCN1 represents the extracellular matrix-associated protein that modulates basic fibroblast growth factor signaling, angiogenesis, and binds to integrin alpha(v)beta(3). The protein is commercially available.

CCN1 belongs to the CCN family, a group of secreted proteins that specifically associate with the extracellular matrix. These CCN proteins show a modular structure and contain up to four distinct functional domains (Leask, A. Abraham, D. J., J. Cell Sci, 2006, 119:4803-10 and Brigstock, D. R., "The CCN family . . . ", Journal of Endocrinology (2003), 178, 169-175).

Surprisingly, it could be found that CCN1 is especially suitable for conditioning implantable tissue matrices, i.e. tissue patches of all kinds, bioartificial implant devices, or bioprosthesises for restitution after an accident or surgical operation to improve their sustainability and longevity upon transplantation. More specifically and preferred, decellularized matrices are used showing reduced immunogenicity against the recipient, preferably a decellularized soft tissue collagen matrix is treated according to the invention.

According to these findings, every molecule with basically the same function with respect to at least the promotion of endothelial cell adhesion can be regarded as equivalent to CCN1. The term "CCN1" as used here refers to CCN1 and functional equivalents thereof, e.g. modifications deviating from the original CCN1 in point mutations, as well as fragments of CCN1, especially those comprising at least one complete functional domain, or constructs with CCN1, for example in connection with transport or carrier molecules or other chemically connected molecules, under the provision that the basic functions of CCN1 with emphasis on cell adhesion are retained.

It can thus also be concluded, that even for other implantable devices than those cited above where a population with endothelial cells, alone or in connection with other diversified cell populations, is expected or intended the coating according to this invention redounds to remarkable advantages. This can for example be the case, if the tissue matrix is artificially constructed from collagen or if a biopolymer is used instead of collagen for the tissue matrix.

Further, the inventive coating may be used in any device for implantation in or proximate to a natural organ or vascular system which is not limited to the specific devices set forth in the examples below.

The invention also encompasses an implantable bioprothesis intended for use in the human body where in-vivo colonization with autologous cells of the recipient, preferably endothelial cells of the recipient is desired and expected, coated with the coating of the invention and a method to produce the same with the following steps:
 a) providing an implantable tissue of animal or human origin;
 b) removing native cells from the tissue or organ to provide a tissue matrix (decellularization);
 c) treating the tissue matrix with the extracellular matrix-associated protein as defined above or a fragment thereof or a construct with that protein with corresponding function with respect to cell adhesion to deposit the protein on a surface of the matrix to produce a coated device.

DETAILED DESCRIPTION OF THE PREFERRED EMBODIMENTS

The coating according to the invention may be accomplished using various techniques to deposit the CCN1 onto or into the substrate, i.e. the implantable device.

According to one aspect of the invention the device, preferably the decellularized bioprosthesis, is dipped or immersed into a solution comprising the CCN1 (CCN1 in the sense as defined above). The CCN1 could also be sprayed to the implant surface or be applied by any other technique known to the practitioner in the field. The solvent may be any suitable fluid, for example a cell culture medium, a physiological solution or the like. After the dipping or immersion in one or several cycles, generally the deposition of the CCN1 on the surface or at least part of the surface of the implant, the coated device is preferably not dried, although a careful drying is not excluded. The CCN1 deposition process leaves the device with a thin film of tightly adherent bioactive molecules, preferably confluent in the plane.

In a preferred embodiment the coating is therefore a humid protein-rich coating.

The implantable device according to this invention is intended for use in the human body where in-vivo repopulation or remodeling with endothelial cells of the recipient is expected or intended and bears a coating comprising CCN1 or a fragment thereof or a construct with CCN1 with corresponding function with respect to cell adhesion and deposited on a surface of the device The device is preferably a prosthetic device what means that a natural tissue or organ or part of organ lost in an accident or surgical operation is replaced.

The prosthetic device can thus be a tissue for implantation, a graft, shunt, vessel, or organ or part of an organ.

In accordance with preferred embodiments of the invention the tissue prosthesis is derived from animal or human origin and comprises a collagen-based tissue matrix.

Further it is preferred that the tissue prosthesis is part of a heart, a heart valve, an artery, a vene, any blood vessel, a pulmonary tissue or an intestinal tissue, especially a vascularized intestinal tissue as disclosed in EP 1 230 939 B1.

For massive reduction in antigeneicity of bioprosthesis native biological tissues have to be completely decellularized. Therefore, the device according to preferred embodiments of this invention comprises decellularized tissue matrices. Decellularization as such, is a process well known in the art, and the skilled practitioner may choose an appropriate technique for the very application.

Preferably decellularization is performed by either enzymatic treatment, osmotic lysis, including hypo- and/or hypertonic treatment, treatment with detergents and/or cell-toxic chemicals, chelating agents, mechanical means or a combination of two or more of these methods.

For enzymatic treatment trypsin/EDTA (0.05%/0.02%) is preferred. For osmotic lysis a treatment with hypotonic (10 mM) and hypertonic (1.5 M KCl) solution in a series is most preferred, and especially a treatment as disclosed in DE 10 2005 023 599 A1. Decellularization with tris buffers, or detergent decellularization with Triton X-100 (0.5%), SDS (0.5%), Na-deoxycholate (0.5%) and others—or any combination of these in any concentration and various incubation temperatures—is successful and appropriate as well.

The process for the production of an implantable and decellularized device according to this invention comprises the following steps:
 a) providing an implantable tissue of animal or human origin;
 b) removing native cells from the tissue or organ to provide a tissue matrix (decellularization);
 c) treating the tissue matrix with CCN1 or a fragment thereof or a construct with CCN1 with corresponding function with respect to cell adhesion to deposit the CCN1 on a surface of the matrix to produce a coated device.

As described above, the treatment of step c) comprises preferably one of the following techniques: immersing or dipping the tissue into a solution of CCN1; rinsing the tissue with a solution of CCN1; spraying a solution of CCN1 to the surface of the tissue, where CCN1 is to be understood in the sense of the definition given above.

The Present Invention Has Several Advantages:

Placement of a thin film, tightly adherent bioactive molecules coating onto the various bioprosthetic devices provides attractive properties to the device for colonization with endothelial cells. As a result, a bioprosthetic device may be used in situations where other devices have been preferred, thus providing more options for the surgeon and the patient. For example, homografts have been the preferred device for replacement of a valve in a patient with active endocarditis. Homografts are in low supply, high demand and are typically reserved for pediatric cases. Thus, having a bioprosthetic device with a bioactive coating provides a significant new option for adult endocarditis cases.

To circumvent the low supply of homografts for pediatric patients, bioprostheic devices of xenogeneic origin with a bioactive coating may serve as an alternative. Furthermore, implantation of bioprosthetic arterio-venous shunts with a bioactive coating in dialysis patients will allow a fast in vivo generation of a living artificial and puncture resistant vessel suited for dialysis.

Although the present invention has been described with reference to preferred embodiments, workers skilled in the art will recognize that changes may be made in form and detail without departing from the spirit and scope of the invention.

For example, even though certain techniques have been disclosed as preferred, other methods including chemical methods for deposition of the coating or mechanical methods for decellularization are within the contemplation of this invention.

Example 1

Ovine PV (pulmonary valves from sheep) were decellularized using detergent solution (0.5%-Na-deoxycholate/0.5%-SDS). The completeness of decellularization was assessed by histological stainings (H&E). Coating of the luminal surface of decellularized PV was performed with 500 ng recombinant CCN1 (ABNOVA (Taiwan) CORPORATION) in 10 mL cell culture medium DMEM for 12 h under slow rotation. Immunostainings revealed a complete coverage of CCN1 on the luminal surface of coated PV.

A efficient repopulation with endothelial cells was demonstrated upon seeding and pulsatile flow cultivation in the bioreactor in vitro. The superiority of these CCN1 coated valves however was found by in vivo testing.

These decellularized and CCN1 coated PV were transplanted into the orthotopic position in juvenile sheep. After three months the function of the valves was evaluated by echocardiography and in all cases (n=4) the valves were fully competent without any signs of leakiness. The histological analysis of the valves after euthanization of the sheep revealed full coverage with an endothelial monolayer covering wall and the ventricular and the pulmonal side of valves leaflets. This in contrast to decellularized but not CCN1 covered valves which lack an in vivo re-endothilalization three months after implantation in the sheep model.

Example 2

The existing vascular bed of a completely decellularized biological vascularized intestinal matrix was filled with a solution of 500 ng recombinant CCN1 (ABNOVA (Taiwan) CORPORATION) in 3 mL EBM-2 medium by injection via the arterial branch of the pedicle. Incubation was performed overnight at 37° C. in completely humidified atmosphere composed of air supplemented with 5% $CO_2$. During this incubation time the biological vascularized matrix was placed in a Petri dish (d=10 cm) containing EBM-2 that prevents the matrix from drying-up. This treatment leads to a complete coating of the walls of the vascular bed as demonstrated by immunohistochemical stains against CCN1.

This method will allow the efficient reseeding with a low number of endothelal cells in vitro prior implantation into the patient.

In summary, the exposure of decellularized matrices to medium containing recombinant CCN1 leads to a coating of the surface with this molecule, which in turn results in adhesion of endothelial cells in vitro when incubated in a bioreactor (example 1 & 2) and in vivo when implanted in orthotopic position in the sheep model (example 1).

The invention claimed is:

1. A coating for an implantable device, said implantable device intended for use in the human body where in-vivo colonization or remodeling of a luminal surface with a layer of endothelial cells which are autologous cells of a recipient is desired, said coating comprising an extracellular matrix-associated protein mediating cell adhesion or cell migration or a fragment thereof deposited on said luminal surface of the device wherein the protein is CCN1.

2. The coating according to claim 1, wherein the coating is a thin film of tightly adherent bioactive molecules.

3. An implantable device intended for use in the human body, wherein said implantable device has deposited on at least one luminal surface an extracellular matrix-associated protein mediating cell adhesion or migration or a fragment thereof wherein the protein is CCN1, said CCN1 being deposited on said at least one luminal surface in a manner that promotes in vivo colonization or remodeling of said at least one luminal surface of said implantable device with autologous cells of a recipient as a layer of endothelial cells.

4. The device according to claim 3, wherein said device is a prosthetic device.

5. The device according to claim 4 wherein the prosthetic device is selected from the group consisting of an implant tissue, a graft, a shunt, a vessel, and an organ or part of an organ.

6. The device according to claim 3, wherein the device is a tissue prosthesis derived from animal or human origin and comprises a collagen-based tissue matrix.

7. The device according to claim 6, wherein the tissue prosthesis is part of a heart, a blood vessel, a pulmonary tissue or an intestinal tissue.

8. The device according to claim 3, wherein the device comprises a decellularized tissue.

9. A process for the production of an implantable device intended for use in the human body, comprising the following steps:
   a) providing an implantable tissue of animal or human origin;
   b) removing native cells from the tissue or organ to provide a tissue matrix;
   c) treating the tissue matrix with CCN1 protein or a fragment thereof by depositing the CCN1 protein or the fragment thereof on a surface of the tissue matrix to produce a coated device where the CCN1 protein or fragment thereof is deposited in a manner sufficient to promote colonization or remodeling of the surface with a layer of endothelial cells.

10. The process according to claim 9, wherein said removing step b) is achieved using one or more of the following techniques:
   enzymatic treatment,
   osmotic lysis including hypotonic and/or hypertonic treatment,
   treatment with detergents,
   treatment with cell-toxic chemicals, and
   mechanical treatment.

11. The process according to claim 9, wherein the treating step c) is performed by one or more of the following techniques: immersing or dipping the tissue into a solution which includes the CCN1 protein or fragment thereof; rinsing the tissue with a solution which includes the CCN1 protein or fragment thereof; and spraying a solution which includes the CCN1 protein or fragment thereof on the surface of the tissue.

12. The coating of claim 1, wherein the extracellular matrix-associated protein mediating cell adhesion or cell migration is connected with a transport or carrier molecule.

13. The device of claim 3, wherein the extracellular matrix-associated protein meditating cell adhesion or cell migration is connected with a transport or carrier molecule.

14. The device of claim 7, wherein said part of a heart is a heart valve.

15. The device of claim 7, wherein said blood vessel is an artery or a vein.

16. The process of claim 9, wherein the CCN1 protein or the fragment thereof is connected to a transport or carrier molecule.

17. The process of claim 9, further comprising the step of d) incubating said coated device with endothelial cells in a bioreactor in a manner that allows adhesion of said endothelial cells to said coated device.

18. An implantable prosthetic device derived from human or animal tissue, comprising:
    a decellularized collagen tissue matrix treated with CCN1 protein or fragment thereof such that a thin film of tightly adherent bioactive molecules of said CCN1 protein or fragment thereof is bound to a surface of said decellularized collagen tissue matrix and is sufficient to be colonized or remodeled by a layer of endothelial cells,
    wherein said implantable prosthetic device is in the form of a tissue selected from the group consisting of pulmonary, intestinal, and cardiac tissues.

19. The implantable prosthetic device of claim 18 wherein said tissue is a cardiac tissue and wherein said cardiac tissue is selected from the group consisting of a heart valve, an artery, and a vein.

20. The implantable prosthetic device of claim 18 wherein the decellularized collagen matrix is of xenogenic origin.

21. An implantable prosthetic device derived from human or animal tissue, comprising:
    a decellularized collagen tissue matrix treated with CCN1 protein or fragment thereof such that a thin film of tightly adherent bioactive molecules of said CCN1 protein or fragment thereof is bound to a surface of said decellularized collagen tissue matrix; and
    a layer of endothelial cells on said surface,
    wherein said implantable prosthetic device is in the form of a tissue selected from the group consisting of pulmonary, intestinal, and cardiac tissues.

22. A method for implanting a device in a subject in need thereof, comprising the steps of:
    removing native cells from a tissue to obtain a decellularized tissue matrix;
    coating at least one surface of said decellularized tissue matrix with a CCN1 protein or fragment thereof to produce a coated tissue matrix;
    colonizing said at least one surface of said coated tissue matrix with a layer of endothelial cells in vitro to produce a tissue matrix colonized with a layer of endothelial cells; and
    implanting said tissue matrix colonized with said layer of endothelial cells in said subject.

* * * * *